US012698263B2

(12) United States Patent
Quinn et al.

(10) Patent No.: US 12,698,263 B2
(45) Date of Patent: Aug. 4, 2026

(54) PROCESS FOR PREPARING 3-AMINO-1-BUTANOL AND RELATED COMPOUNDS

(71) Applicant: Advancion Corporation, Buffalo Grove, IL (US)

(72) Inventors: Jordan Quinn, Long Grove, IL (US); Shengwen Yuan, Northbrook, IL (US)

(73) Assignee: Advancion Corporation, Buffalo Grove, IL (US)

( * ) Notice: Subject to any disclaimer, the term of this patent is extended or adjusted under 35 U.S.C. 154(b) by 337 days.

(21) Appl. No.: 18/383,450

(22) Filed: Oct. 24, 2023

(65) Prior Publication Data

US 2024/0158358 A1 May 16, 2024

Related U.S. Application Data

(60) Provisional application No. 63/419,979, filed on Oct. 27, 2022.

(51) Int. Cl.
*C07D 261/04* (2006.01)

(52) U.S. Cl.
CPC .................................. *C07D 261/04* (2013.01)

(58) Field of Classification Search
CPC .................................................... C07D 261/04
See application file for complete search history.

(56) References Cited

U.S. PATENT DOCUMENTS 5,859,247 A * 1/1999 Curran .................... C07B 63/02
585/800

FOREIGN PATENT DOCUMENTS

| | | | | |
|---|---|---|---|---|
| CN | 104370755 A | 2/2015 | | |
| WO | WO-2008008539 A2 * | 1/2008 | ................ | A61P 7/10 |
| WO | WO-2020/094528 A1 | 5/2020 | | |

OTHER PUBLICATIONS

Kozikowski, Journal of Organic Chemistry (1985), 50(6), 778-85.*
Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
Registry/Zregistry (CAS Registrysm) Sep. 2016 2 pages.*
Brasholz Aust. J. Chem. 2011, 64, 1397-1401.*
Brown et al., "Reactions of Nitrile Oxides With Phenylsulphinylpropa-1,2, Diene and 1-Phenylthioprop-2-ENE. New Routes to Functionalised a,ß-Unsaturated Ketone Equivalents," Synthetic Communications, 15(7):633-642 (Jun. 5, 1985).
Hilpert et al., "ß-Secretase (BACE1) inhibitors with high in vivo efficacy suitable for clinical evaluation in Alzheimer's disease," Journal of Medicinal Chemistry, 56(10):3980-3995 (May 23, 2013).
International Search Report and Written Opinion on PCT/US2023/035827 dated Feb. 2, 2024, 11 pages.
Kantorowski et al., "Use of Diisocyanates for in Situ Preparation of Nitrile Oxides:? Preparation of Isoxazoles and Isoxazolines", The Journal of Organic Chemistry, 63(15):5272-5274 (Jul. 1, 1998).

* cited by examiner

*Primary Examiner* — Nizal S Chandrakumar
(74) *Attorney, Agent, or Firm* — Foley & Lardner LLP

(57) ABSTRACT

Disclosed herein are methods and processes of preparing 3-amino-($C_{3-6}$)-alkan-1-ol, including optically active 3-amino-($C_{3-6}$)-alkan-1-ol (e.g., optically active 3-amino-1-butanol such as (R)-3-amino-1-butanol). The 3-amino-($C_{3-6}$)-alkan-1-ol may be optionally substituted at the 1-position, e.g., with OH, alkoxy, O-acetyl, or silyl groups, among others. The processes include contacting a 1-nitro-($C_{1-4}$)-alkane with a vinyl source or an acetylene source in the presence of a base and a dehydrating agent to provide 3-($C_{0-3}$)-alkyl-2-isoxazoline; and/or contacting the 3-($C_{0-3}$)-alkyl-2-isoxazoline with hydrogen and a hydrogenation catalyst to provide 3-amino-($C_{3-6}$)-alkan-1-ol.

11 Claims, No Drawings

PROCESS FOR PREPARING 3-AMINO-1-BUTANOL AND RELATED COMPOUNDS

CROSS-REFERENCE TO RELATED APPLICATION

This application claims the benefit of and priority to U.S. Patent Application No. 63/419,979, filed on Oct. 27, 2022, the contents of which are incorporated herein by reference in its entirety.

TECHNICAL FIELD

The present disclosure relates generally to methods for preparing 3-amino-($C_{3-6}$)-alkan-1-ol, including optically active 3-amino-($C_{3-6}$)-alkan-1-ol (e.g., optically active 3-amino-1-butanol such as (R)-3-amino-1-butanol).

BACKGROUND (R)-3-amino-1-butanol is a key intermediate in the manufacture of the antibiotic dolutegravir. While methods for producing 3-amino-1-butanol (including (R)-3-amino-1-butanol) have been described, these methods involve lengthy syntheses, expensive reduction processes, and substantial waste generation. Therefore, new and environmental friendly methods are desirable to manufacture 3-amino-1-butanol, including optically active 3-amino-1-butanol such as (R)-3-amino-1-butanol, with improved efficiency and reduced costs.

SUMMARY

The present technology is based, in part, on the surprising discovery that 3-amino-($C_{3-6}$)-alkan-1-ol (e.g., 3-amino-1-butanol), including optically active 3-amino-($C_{3-6}$)-alkan-1-ol (e.g., an optically active 3-amino-1-butanol such as (R)-3-amino-1-butanol), can be manufactured using the methods described herein.

In one aspect, disclosed herein is a process comprising contacting a 1-nitro-($C_{1-4}$)-alkane with a vinyl source or an acetylene source in the presence of a base and a dehydrating agent to provide a product selected from optionally 5-substituted 3-($C_{0-3}$)-alkyl-2-isoxazoline or optionally 5-substituted 3-($C_{0-3}$)-alkyl-2-isoxazole.

In some embodiments, the process further comprises contacting the product (optionally 5-substituted 3-($C_{0-3}$)-alkyl-2-isoxazoline or optionally 5-substituted 3-($C_{0-3}$)-alkyl-2-isoxazole) with a reducing agent to provide a reduced product selected from an optionally 5-substituted 3-($C_{0-3}$)-alkyl-2-isoxazolidine or an optionally 1-substituted 3-amino-($C_{3-6}$)-alkan-1-ol. In some embodiments, the reducing agent is hydrogen and a hydrogenation catalyst to provide optionally 1-substituted 3-amino-($C_{3-6}$)-alkan-1-ol, e.g., 3-amino-butan-1-ol.

In another aspect, disclosed herein is a composition (e.g., a composition prepared according to any method described herein), wherein the composition comprises (R)-3-($C_{0-3}$)-alkylisoxazolidine and has an (R)/(S) enantiomeric ratio of greater than 1.00 (R)-3-($C_{0-3}$)-alkylisoxazolidine: (S)-3-($C_{0-3}$)-alkylisoxazolidine, e.g., (R)-3-methylisoxazolidine: (S)-3-methylisoxazolidine.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

DETAILED DESCRIPTION

Definitions

The following terms are used throughout as defined below.

As used herein and in the appended claims, singular articles such as “a” and “an” and “the” and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the embodiments and does not pose a limitation on the scope of the claims unless otherwise stated. No language in the specification should be construed as indicating any non-claimed element as essential.

All temperatures are in degrees Celsius (° C.) unless otherwise specified.

Isolated: As used herein, the term “isolated” refers to a substance and/or entity that has been (1) separated from at least some of the components with which it was associated when initially produced (whether in nature and/or in an experimental setting), and/or (2) synthetically produced, prepared, and/or manufactured (i.e., not a product of nature). In some embodiments, isolated agents are about 80%, about 85%, about 90%, about 91%, about 92%, about 93%, about 94%, about 95%, about 96%, about 97%, about 98%, about 99%, or more than about 99% pure or a range between and including any two of the foregoing values. As used herein, a substance is “pure” if it is substantially free (e.g., contains less than 5 wt %, 4 wt %, 3 wt %, 2 wt %, or 1 wt %) of other components. As used herein, calculation of percent purity of isolated substances and/or entities do not include excipients (e.g., buffer, solvent, water, etc.).

Approximately or about: As used herein, the term “approximately” or “about”, as applied to one or more values of interest, refers to a value that is similar to a stated reference value. In certain embodiments, the term “approximately” or “about” refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used in the description and the appended claims, the singular forms “a”, “an”, and “the” include plural referents unless the context clearly dictates otherwise. Thus, for example, reference to “a composition” includes mixtures of two or more such compositions.

“Optional” or “optionally” means that the subsequently described event or circumstance may or may not occur, and that the description includes instances where the event or circumstance occurs and instances where it does not.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

"Stereoselective," "enantioselective," "diastereoselective," and variants thereof, refer to a given process (e.g., ester hydrolysis, hydrogenation, hydroformylation, palladium coupling, hydrosilation, hydrocyanation, olefin metathesis, hydroacylation, allylamine isomerization, etc.) that yields more of one stereoisomer, enantiomer, or diastereoisomer than of another, respectively.

"Stereoisomerically enriched," "enantiomerically enriched," "diastereomerically enriched," and variants thereof, refer, respectively, to a sample of a compound that has more of one stereoisomer, enantiomer or diastereomer than another. The degree of enrichment may be measured by % of total product, or for a pair of enantiomers or diastereomers, by ee or de.

"Substantially pure stereoisomer," "substantially pure enantiomer," "substantially pure diastereomer," and variants thereof, refer, respectively, to a sample containing a stereoisomer, enantiomer, or diastereomer, which comprises at least about 95% of the sample. For pairs of enantiomers and diastereomers, a substantially pure enantiomer or diastereomer would correspond to samples having an ee or de of about 90% or greater.

A "pure stereoisomer," "pure enantiomer," "pure diastereomer," and variants thereof, refer, respectively, to a sample containing a stereoisomer, enantiomer, or diastereomer, which comprises at least about 99.5% of the sample. For pairs of enantiomers and diastereomers, a pure enantiomer or pure diastereomer" would correspond to samples having an ee or de of about 99% or greater.

Solvate: can include, but is not limited to, a solvate that retains one or more of the activities and/or properties of the compound and that is not undesirable. Examples of solvates include, but are not limited to, a compound in combination with water, isopropanol, ethanol, methanol, DMSO, ethyl acetate, acetic acid, ethanolamine, or combinations thereof.

Solvent: can include, but is not limited to, non-polar, polar aprotic, and polar protic solvents. Illustrative examples of non-polar solvents include, but are not limited to, pentane, cyclopentane, hexane, cyclohexane, benzene, toluene, xylene, 1,4-dioxane, chloroform, diethyl ether, and dichloromethane (DCM). Illustrative examples of polar aprotic solvents include, but are not limited to, tetrahydrofuran (TRF), ethyl acetate, isopropyl acetate (IPAc), acetone, dimethylformamide (DMF), dimethyl acetamide (DMAc), acetonitrile (MeCN), butyronitrile, dimethyl sulfoxide (DMSO), nitromethane, and propylene carbonate. Illustrative examples of polar protic solvents include, but are not limited to, formic acid, n-butanol, isopropanol (IPA), n-propanol, ethanol, methanol, acetic acid, and water.

Acid: refers to molecules or ions capable of donating a hydrogen (proton or hydrogen ion $H^+$), or, alternatively, capable of accepting an electron pair (e.g., a Lewis acid). Acids can include, but are not limited to, mineral acids, sulfonic acids, carboxylic acids, halogenated carboxylic acids, and vinylogous carboxylic acids.

Base: as used herein, "base" refers to a compound that can accept a proton or donate a lone electron pair. Examples of bases include, alkali ($OH^-$), carbonate, bicarbonate, alkoxides (alkyl-O($^-$)), hydrides (alkali metal hydrides and $CaH_2$), metal amides, and neutral nitrogen containing bases such as trialkylamines (e.g., triethylamine) and heteraromatics (e.g., pyridine, imidazole) and the like.

Organic base: as used herein, "organic base" refers to a carbon containing compound having one or more functional groups capable of accepting a proton from an acid group. For example, the organic base may contain a basic nitrogen such an amine group or an aromatic ring nitrogen. Exemplary organic bases include trimethylamine, triethylamine, benzyldiethylamine, dimethylethylamine, imidazole, pyridine, piperidine, and the like.

Dehydrating agent: as used herein, "dehydrating agent" refers to an agent or a compound capable of removing water molecules in a chemical reaction.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

Alkanes and alkyl groups respectively refer to saturated straight chain and branched chain hydrocarbons and hydrocarbon groups having (unless otherwise specified) from 1 to 12 carbon atoms, or, in some embodiments, from 1 to 10, from 1 to 8, 1 to 6, or 1 to 4 carbon atoms. Examples of straight chain alkane/alkyl groups include methane/methyl, ethane/ethyl, n-propane/n-propyl, n-butane/n-butyl, n-pentane/n-pentyl, and n-hexane/n-hexyl. Examples of branched alkane/alkyl groups include, but are not limited to, isopropane/isopropyl, isobutane/iso-butyl, and 2,2-dimethylpropane/2,2-dimethylpropyl. Alkanes/alkyl groups may be substituted with one, two or three substituents such as, e.g., nitro, hydroxy, and halo (F, Cl, Br, I).

Salts of compounds described herein are within the scope of the present technology and include acid or base addition salts. When the compound of the present technology has a basic group, such as, for example, an amino group, salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$) ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as “up to,” “at least,” “greater than,” “less than,” and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Methods of the Present Technology

Disclosed herein are methods and processes of preparing 3-amino-($C_{3-6}$)-alkan-1-ols (e.g., 3-amino-1-butanol) and 1-substituted 3-amino-($C_{3-6}$)-alkan-1-ols, including optically active optionally 1-substituted 3-amino-($C_{3-6}$)-alkan-1-ol s (e.g., optically active 3-amino-1-butanol such as (R)-3-amino-1-butanol), as well as intermediates thereof (e.g., 3-($C_{0-3}$)-alkyl-2-isoxazoline such as 3-methyl-2-isoxazoline). In certain embodiments, the processes disclosed herein can take place concurrently, in a sequential order as described herein, or in any possible order thereof.

Formation of Optionally 5-Substituted 3-($C_{0-3}$)-alkyl-2-isoxazoline

In one aspect, the present disclosure provides a process comprising contacting a 1-nitro-($C_{1-4}$)-alkane (e.g., nitroethane) with a vinyl source or an acetylene source in the presence of a base and a dehydrating agent to provide a product selected from optionally 5-substituted 3-($C_{0-3}$)-alkyl-2-isoxazoline (e.g., 3-methyl-2-isoxazoline) or optionally 5-substituted 3-($C_{0-3}$)-alkyl-2-isoxazole. In any embodiments, the product is selected from 3-($C_{0-3}$)-alkyl-2-isoxazoline (e.g., 3-methyl-2-isoxazoline) or 3-($C_{0-3}$)-alkyl-2-isoxazole.

The vinyl source may be any compound that serves as a source of ethylene or vinyl-containing compounds. The acetylene source may likewise serve as a source of acetylene or alkyne-containing compounds. In any embodiments, the vinyl source and/or the acetylene source may include 2-6 carbon atoms (i.e., 2, 3, 4, 5, or 6 carbon atoms). Non-limiting examples of a vinyl source and an acetylene source include ethylene, acetylene, vinyl acetate, vinyl ethers, and trimethylsilyl acetylene.

In some embodiments, the vinyl source is ethylene, which is used directly in a process described herein to react with 1-nitro-($C_{1-4}$)-alkane to produce the corresponding cycloaddition product (e.g., the 3-($C_{0-3}$)-alkyl-2-isoxazoline product). In some embodiments, a vinyl compound or an acetylene compound such as vinyl acetate, vinyl ethers, acetylene, or trimethylsilyl acetylene is used in a process described herein to react with 1-nitro-($C_{1-4}$)-alkane to produce the corresponding cycloaddition product (e.g., the 3-($C_{0-3}$)-alkyl-2-isoxazoline product or the 3-($C_{0-3}$)-alkylisoxazole product). In some embodiments, the alkyl is a $C_1$ alkyl and the cycloaddition product is a compound having the following structure:

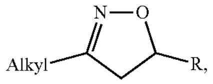
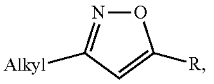

where Alkyl is a $C_{1-3}$ alkyl group, and R is H or a substituent. In some embodiments, R is —OC(O)Me, —O—($C_{1-3}$)-alkyl, H, OH or trimethylsilyl. Accordingly, it should be appreciated that the 3-($C_{0-3}$)-alkyl-2-isoxazoline or 3-($C_{0-3}$)-alkylisoxazole described herein includes optionally 5-substituted 3-($C_{0-3}$)-alkyl-2-isoxazoline (e.g., optionally substituted with an R group) or optionally 5-substituted 3-($C_{0-3}$)-alkylisoxazole (e.g., optionally substituted with an R group).

In some embodiments, the cycloaddition product (e.g., the 3-($C_{0-3}$)-alkyl-2-isoxazoline product or the 3-($C_{0-3}$)-alkylisoxazole product) can be subject to further processes (e.g., a process described herein) to provide 3-amino-($C_{3-6}$)-alkan-1-ol.

In some embodiments, the 1-nitro-($C_{1-4}$)-alkane is nitromethane, nitroethane, 1-nitropropane or 1-nitrobutane. In some embodiments, the 1-nitro-($C_{1-4}$)-alkane is nitroethane and, e.g., the product is selected from optionally 5-substituted 3-methyl-2-isoxazoline or optionally 5-substituted 3-methyl-2-isoxazole. In some embodiments, the product is 3-($C_{0-3}$)-alkyl-2-isoxazoline, e.g., 3-methyl-2-isoxazoline. In some embodiments, the product is 3-($C_{0-3}$)-alkyl-2-isoxazoline, e.g., 3-ethyl-2-isoxazoline.

In some embodiments, the base is an organic base. For example, the organic base used in a process described herein may be trimethylamine or triethylamine. In some embodiments, the base (e.g., the organic base) and 1-nitro-($C_{1-4}$)-alkane (e.g., nitroethane) are present at a molar ratio (base: 1-nitro-($C_{1-4}$)-alkane) ranging from about 0.1:100 to about 20:100, e.g., at about any of the following ratios or a range between and including such ratios: 0.1:100, 0.2:100, 0.3:100, 0.4:100, 0.5:100, 0.75:100, 1:100, 1.5:100, 2:100, 2.5:100, 3:100, 4:100, 5:100, 6:100, 8:100, 10:100, 12.5:100, 15:100, and 20:100. Thus, the base and 1-nitro($C_{1-4}$) alkane may be present at a molar ratio from about 0.5:100 or about 1:100 to about 15:100, or from about 1:100 to about 6:100.

In some embodiments, the dehydrating agent used in a process described herein may be isocyanates, such as phenyl isocyanate or toluene diisocyanate. In some embodiments, the dehydrating agent used in a process described herein may be anhydrides, such as acetic anhydride or phthalic anhydride. In some embodiments, the dehydrating agent used in a process described herein may be chlorides, such as phosphorous oxychloride, ethyl chloroformate, or thionyl chloride. In some embodiments, the dehydrating agent (e.g., an isocyanate such as phenyl isocyanate, toluene diisocyanate, or an anhydride such as acetic anhydride or phthalic anhydride (e.g. hexahydrophthalic anhydride) and 1-nitro-($C_{1-4}$)-alkane (e.g., nitroethane) are present with a molar ratio (dehydrating agent: 1-nitro-($C_{1-4}$)-alkane) of from about 1:1 to about 5:1. Representative ratios thus include at about any of the following: 1:1, 1.5:1, 2:1, 2.5:1, 3:1, 3.5:1, 4:1, 4.5:1, 5:1, or a range between and including any two of the foregoing ratios. For example, the molar ratio of dehydrating agent to 1-nitro-($C_{1-4}$)-alkane therefore may also be from about 1:1 to about 2:1.

In some embodiments, the contacting (e.g., contacting a 1-nitro-($C_{1-4}$)-alkane with a vinyl source or an acetylene source) occurs in the presence of a solvent. In some embodiments, the solvent is a non-polar solvent, such as an aromatic solvent. In some embodiments, the solvent may be benzene, toluene, xylene, or any combination of two or more thereof.

In some embodiments, the contacting described herein (e.g., contacting a 1-nitro-($C_{1-4}$)-alkane with a vinyl source or an acetylene source) occurs at a pressure of about 1-about 500 psi, including for example, about any of 1, 5, 10, 25, 50, 75, 100, 150, 200, 250, 300, 350, 400, 450, or 500 psi or a range between and including any two of the foregoing values. Hence, in some embodiments, the pressure is about 100-about 350 psi, or about 200-about 250 psi.

In some embodiments, the contacting described herein (e.g., contacting a 1-nitro-($C_{1-4}$)-alkane with a vinyl source or an acetylene source) occurs at an elevated temperature. For example, the contacting may occur at about 40-about 70° C. Representative temperatures include any of about 40° C., 45° C., 50° C., 55° C., 50° C., 65° C., 70° C., or a range between and including any two of the foregoing values. Hence in some embodiments, the temperature range may be about 55-about 65° C., or about 50-about 60° C.

As described above, the process can provide 3-($C_{0-3}$)-alkyl-2-isoxazoline (e.g., 3-methyl-2-isoxazoline). In some embodiments, the process further comprises isolating and/or purifying the obtained optionally 5-substituted 3-($C_{0-3}$)-alkyl-2-isoxazoline or optionally 5-substituted 3-($C_{0-3}$)-alkyl-2-isoxazole from the reaction mixture. For example, the process may comprise one or more of filtering the reaction mixture, washing the obtained filter cake (e.g., washing with a poor solvent such as hexane), and distilling the filtrate.

In some embodiments, the process described herein provides optionally 5-substituted 3-($C_{0-3}$)-alkyl-2-isoxazoline (e.g., 3-methyl-2-isoxazoline) or optionally 5-substituted 3-($C_{0-3}$)-alkyl-2-isoxazole in at least about 30%, at least about 50%, at least about 60%, at least about 70%, at least about 80%, or at least about 90% yield.

Formation of Optionally 1-Substituted 3-amino-($c_{3-6}$)-alkan-1-Ol

In some embodiments, the process described herein further comprises converting 3-($C_{0-3}$)-alkylisoxazole or 3-($C_{0-3}$)-alkyl-2-isoxazoline (e.g., 3-methyl-2-isoxazoline) to 3-amino-($C_{3-6}$)-alkan-1-ol (e.g., 3-amino-1-butanol). Accordingly, the present disclosure also provides processes for preparing 3-amino-($C_{3-6}$)-alkan-1-ol (e.g., 3-amino-1-butanol).

In some embodiments, the 3-($C_{0-3}$)-alkylisoxazole is a compound having the following structure:

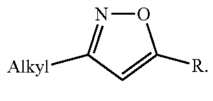

In some embodiments, the 3-($C_{0-3}$)-alkyl-2-isoxazoline is a compound having the following structure:

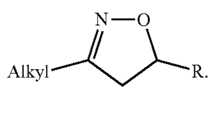

Accordingly, it should be appreciated that the 3-($C_{0-3}$)-alkylisoxazolidine described herein includes optionally 5-substituted 3-($C_{0-3}$)-alkylisoxazolidine having, e.g., the following structure (including enantiomers thereof):

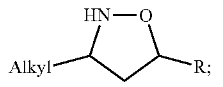

and the 3-amino-($C_{3-6}$)-alkan-1-ol described herein includes optionally 1-substituted 3-amino-($C_{3-6}$)-alkan-1-ol having the following structure (including enantiomers thereof):

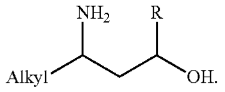

In the foregoing embodiments, Alkyl is a $C_{1-3}$ alkyl group, e.g., a methyl group. In some embodiments, R is —OC(O)Me, —O—($C_{1-3}$)-alkyl, H, OH, or trimethylsilyl.

In some embodiments, the process described herein may include converting a 3-($C_{0-3}$)-alkylisoxazole to the corresponding 3-($C_{0-3}$)-alkyl-2-isoxazoline in the presence of reducing agents (e.g., boranes, metal hydrides, silanes, hydrogen with a hydrogenation catalyst). In some embodiments, the 3-($C_{0-3}$)-alkylisoxazole is converted to the corresponding 3-amino-($C_{3-6}$)-alkan-1-ol directly.

Similarly, the 3-($C_{0-3}$)-alkyl-2-isoxazoline from the first step or from the 3-($C_{0-3}$)-alkylisoxazole may be reduced to the corresponding 3-amino-($C_{3-6}$)-alkan-1-ol using any suitable reducing agent, including those disclosed herein. In particular, catalytic hydrogenation may be used to reduce the 3-($C_{0-3}$)-alkyl-2-isoxazoline.

In some embodiments, the 3-($C_{0-3}$)-alkyl-2-isoxazoline is converted to the corresponding 3-amino-($C_{3-6}$)-alkan-1-ol directly. In some embodiments, the 3-($C_{0-3}$)-alkyl-2-isoxazoline is converted to the corresponding 3-amino-($C_{3-6}$)-alkan-1-ol through a 3-($C_{0-3}$)-alkylisoxazolidine intermediate.

In some embodiments, the process described herein comprises contacting the 3-($C_{0-3}$)-alkyl-2-isoxazoline (e.g., 3-methyl-2-isoxazoline) with hydrogen and a hydrogenation catalyst (e.g., in a reactor) to provide 3-amino-($C_{3-6}$)-alkan-1-ol (e.g., 3-amino-1-butanol). In some embodiments, the process described herein comprises contacting the 3-($C_{0-3}$)-alkyl-2-isoxazoline (e.g., 3-methyl-2-isoxazoline) with hydrogen and a hydrogenation catalyst (e.g., in a reactor) to provide 3-($C_{0-3}$)-alkylisoxazolidine, which is then converted to 3-amino-($C_{3-6}$)-alkan-1-ol (e.g., 3-amino-1-butanol) in the presence of a reducing agent.

In some embodiments, the 3-($C_{0-3}$)-alkyl-2-isoxazoline is 3-methyl-2-isoxazoline. In some embodiments, the 3-amino-($C_{3-6}$)-alkan-1-ol is 3-amino-1-butanol.

In some embodiments, the contacting described herein (e.g., contacting the 3-($C_{0-3}$)-alkyl-2-isoxazoline with hydrogen and a hydrogenation catalyst) occurs in the presence of a solvent. For example, the contacting may occur in the presence of an alcohol such as MeOH. In some embodiments, the contacting (e.g., contacting the 3-($C_{0-3}$)-alkyl-2-isoxazoline with hydrogen) occurs at an elevated temperature. For example, the contacting may occur at a temperature of about 20-100° C., about 50-80° C. or about 60-70° C. for a time period (e.g., about 1-48 hours). In some embodiments, the hydrogen is present at a pressure of about 10-2500 psi, 50-900 psi, about 500-900 psi, or about 600-800 psi.

In some embodiments, the hydrogenation catalyst used in the process described herein is not an optically active catalyst, and the corresponding 3-amino-($C_{3-6}$)-alkan-1-ol product is racemic 3-amino-($C_{3-6}$)-alkan-1-ol (e.g., racemic 3-amino-1-butanol). For example, the hydrogenation catalyst may be Raney nickel or a palladium catalyst. In some embodiments, the hydrogenation catalyst (e.g., Raney nickel) and 3-($C_{0-3}$)-alkyl-2-isoxazoline (e.g., 3-methyl-2-isoxazoline) are present with a molar ratio (hydrogenation catalyst: 3-($C_{0-3}$)-alkyl-2-isoxazoline) ranging from about 1:100 to about 20:100, or about 15:100 to about 20:100.

In some embodiments, the hydrogenation catalyst used in the process described herein is an optically active catalyst, and the corresponding hydrogenation product (e.g., 3-($C_{0-3}$)-alkylisoxazolidine or 3-amino-($C_{3-6}$)-alkan-1-ol product) is enriched in one enantiomer (e.g., (R)-enantiomer enriched). In some embodiments, the (R)-enantiomer enriched hydrogenation product (e.g., 3-($C_{0-3}$)-alkylisoxazolidine or 3-amino-($C_{3-6}$)-alkan-1-ol) has an enantiomeric ratio ((R)-enantiomer: (S)-enantiomer) of greater than 1:1, great than 3:1, greater than 5:1, greater than 10:1, greater than 20:1, or greater than 50:1. In some embodiments, the optically active hydrogenation catalyst is a metal catalyst having a formula of Mtn. In some embodiments, M is or comprises iridium, rhodium, ruthenium, nickel, or other transition metals. In some embodiments, each L is independently a chiral ligand. In some embodiments, n is an integer of 1-4 (e.g., n is 1, 2, 3, or 4). In some embodiments, the hydrogenation catalyst (e.g., $ML_n$) and 3-($C_{0-3}$)-alkyl-2-isoxazoline (e.g., 3-methyl-2-isoxazoline) are present with a molar ratio (hydrogenation catalyst: 3-($C_{2-6}$)-alkyl-2-isoxazoline) ranging from about 1:100 to about 20:100, or about 15:100 to about 20:100 (e.g., about 1:, 2:, 3:, 4:, 5:, 6:, 7:, 8:, 9:, 10:, 11:, 12:, 13:, 14:, 15:, 16:, 17:, 18:, 19:, or 20:100, or a range between and including any two of the foregoing values.

In some embodiments, the enantiomer enriched hydrogenation product is 3-($C_{0-3}$)-alkylisoxazolidine, which has an enantiomeric ratio ((R)-3-($C_{0-3}$)-alkylisoxazolidine: (S)-3-($C_{0-3}$)-alkylisoxazolidine) of greater than 1:1, great than 3:1, greater than 5:1, greater than 10:1, greater than 20:1, or greater than 50:1. In some embodiments, the enantiomer enriched hydrogenation product is 3-amino-($C_{3-6}$)-alkan-1-ol, which has an enantiomeric ratio ((R)-3-amino-($C_{3-6}$)-alkan-1-ol: (S)-3-amino-($C_{3-6}$)-alkan-1-ol) of greater than 1:1, great than 3:1, greater than 5:1, greater than 10:1, greater than 20:1, or greater than 50:1. The optical purity may be further improved by chiral chromatography and/or diastereomeric salt recrystallization method.

In some embodiments, the 3-($C_{0-3}$)-alkyl-2-isoxazoline is converted to an enantiomer enriched (e.g., (R)-enantiomer enriched) 3-amino-($C_{3-6}$)-alkan-1-ol in the presence of an optically active reducing agent (e.g., boranes, metal hydrides, silanes, hydrogen), including an optically active boron-containing reagent. For example, WO2020094528A1 discloses methods for reducing carbon-nitrogen double bonds in substituted oximes. Optically active boron-containing reduction catalysts such as oxazaborolidines can be used to reduce oxime ethers to optically active amines. In some embodiments, the optically active boron-containing reagent is present in an amount of about 0-0.5, about 0.5-1, about 1-3, or about 3-5 equivalents (e.g., molar equivalents) relative to 3-($C_{2-6}$)-alkyl-2-isoxazoline.

As described above, the process can provide 3-amino-($C_{3-6}$)-alkan-1-ol (e.g., 3-amino-1-butanol). In some embodiments, the process further comprises isolating and/or purifying the obtained 3-amino-($C_{3-6}$)-alkan-1-ol from the reaction mixture. For example, the process may comprise one or more of filtering the reaction mixture, washing the obtained filter case (e.g., washing with a poor solvent), and distilling the filtrate.

In some embodiments, the process further comprises separating the (R)- and (S)-enantiomers such as the (R)- and (S)-enantiomers of the 3-amino-($C_{3-6}$)-alkan-1-ol, or the (R)- and (S)-enantiomers of 3-($C_{0-3}$)-alkylisoxazolidine (e.g., the (R)- and (S)-enantiomers prepared with a process described herein). Representative separating methods are described herein. For example, 3-amino-($C_{3-6}$)-alkan-1-ol may be separated into (R)-3-amino-($C_{3-6}$)-alkan-1-ol and (5)-3-amino-($C_{3-6}$)-alkan-1-ol by means of chiral chromatography and/or diastereomeric salt recrystallization. In some embodiments, 3-amino-($C_{3-6}$)-alkan-1-ol is separated into (R)- and (S)-enantiomers using diastereomeric salt recrystallization comprising neutralizing 3-amino-($C_{3-6}$)-alkan-1-ol with a chiral acid and separating the resulting diastereomers by crystallization. The optically enriched 3-amino-($C_{3-6}$)-alkan-1-ol can be isolated after treating the salt with a base. The crystallization process may be repeated several times to achieve the desired optical purity. A representative chiral separation method is provided in U.S. Pat. No. 9,115,052B2.

In some embodiments, the process described herein provides 3-amino-($C_{3-6}$)-alkan-1-ol (e.g., 3-amino-1-butanol) in at least about 50%, at least about 60%, at least about 70%, at least about 80%, or at least about 90% yield.

Either step or both steps of the process disclosed herein may be carried out in a batch, semi-batch or continuous fashion using equipment and techniques known in the art.

The examples herein are provided to illustrate advantages of the present technology and to further assist a person of ordinary skill in the art with preparing or using the present technology. The examples herein are also presented in order to more fully illustrate certain aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology

EXAMPLES

General Methods.

Example 1—Synthesis of 3-methyl-2-isoxazoline Using Phenyl Isocyanate

A 1 L Parr reactor was charged with phenyl isocyanate (119.2 g, 1.0 mol), triethylamine (2.02 g, 0.02 mol), and benzene (190 g). The reactor was pressure purged several times with nitrogen and then pressurized with ethylene to 220 psi with mixing. The mixture was heated to 50° C. Nitroethane (47.5 g, 0.626 mol) was fed into the reactor at a rate of 2.25 mL/min. The temperature of the reaction mixture increased to 58° C. during addition. Upon complete addition, the mixture was stirred at 55 to 60° C. for 1 hour. The mixture was cooled to room temperature and vented. The reaction mixture was filtered, and the filter cake was washed. The filtrate was distilled to provide 30 g (70% yield) of 3-methyl-2-isoxazoline (99.1% purity by GC-FID). NMR data supported the assigned structure. 1H NMR (500 MHz, $CDCl_3$) δ: 4.31-4.25 (m, 2H), 2.95-2.89 (m, 2H), 2.01 (s, 3H). 13C NMR (500 MHz, $CDCl_3$) δ: 155.5, 68.2 39.0, 13.0.

Example 2—Synthesis of 3-methyl-2-isoxazoline Using Toluene Diisocyanate

A 500 mL 3-neck round bottom flask was charged with benzene (100 g), toluene diisocyanate (17.42 g, 0.10 mol), and triethylamine (0.4 g 0.004 mol). The mixture was stirred and ethylene was bubbled through the mixture for 10 minutes at room temperature. Nitroethane (7.507 g, 0.10 mol) was added dropwise into the mixture during one hour while maintaining the ethylene flow. After addition of nitroethane was completed, bubbling of ethylene was continued for 3 hours. The mixture was stirred at ambient temperature for 18 hours. GC-FID analysis indicated 58% conversion of nitroethane to 3-methyl-2-isoxazoline.

Example 3. Synthesis of 3-methyl-2-isoxazoline Using Hexahydrophthalic Anhydride A 1 L Parr reactor was charged with hexahydrophthalic anhydride (77.08 g, 0.5 mol), benzene (100 g), and nitroethane (37.54 g, 0.5 mol). The reactor then was sealed and mixing was started. The reactor was purged with 30 psi nitrogen 4 times. The reactor was pressurized with ethylene to 270 psi. The reaction mixture was heated to 65° C. A solution of triethylamine (51.6 g, 0.51 mol) containing 4-dimethylaminopyridine (1.0 g, 0.082 mol) was fed into the reactor at 3 mL/min. After heating for 16 hours at 65° C., GC-FID analysis indication the conversion was 17%. The reaction mixture was further heated to 80° C. for 4 hours. 3-Methyl-2-isoxazoline was collected through distillation of the reaction mixture and the isolated amount was 12 g (30% yield).

Example 4. Synthesis of 3-amino-1-butanol from 3-methyl-2-isoxazoline

A 1 L Parr reactor was charged with 100 g of methanol and 5 g of Raney® nickel. The reactor was pressure purged three times with nitrogen and then with hydrogen. The reaction mixture was heated to 65° C. and pressurized with hydrogen to 700 psi. A solution of 3-methyl-2-isoxazoline (30 g, 0.35 mol) in 30 mL methanol and was fed into the reactor at a rate of 3 mL/min. After complete addition, the reaction mixture was held at 65° C. for 30 minutes. The mixture was cooled to room temperature, vented to atmospheric pressure, and the catalyst was removed by filtration. The filtrate was distilled to provide 18.9 g (60% yield) of 3-amino-1-butanol. NMR data supported the assigned structure. $^{1}H$ NMR (500 MHz, $CDCl_3$) δ: 3.81-3.71 (m, 2H), 3.13-3.09 (m, 1H), 2.81 (b, 3H), 1.64-1.57 (m, 1H), 1.53-1.44 (m, 1H), 1.13-1.11 (m, 3H). $^{13}C$ NMR (500 MHz, $CDCl_3$) δ: 61.9, 47.5 39.6, 25.5.

EQUIVALENTS

While certain embodiments have been illustrated and described, a person with ordinary skill in the art, after reading the foregoing specification, can effect changes, substitutions of equivalents and other types of alterations to the compositions of the present technology as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, or compositions, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Thus, e.g., the use of the terms "comprising," "including," "containing," etc. shall be understood to disclose embodiments using the terms "consisting essentially of" and "consisting of." The phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the technology. This includes the generic description of the technology with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A process comprising contacting nitroethane with ethylene in the presence of base triethylamine and dehydrating agent phenyl isocyanate to provide 3-methyl-2-isoxazoline.

2. The process of claim 1, wherein a molar ratio of the base triethylamine to nitroethane ranges from about 0.1:100 to about 20:100.

3. The process of claim 1, wherein a molar ratio of the dehydrating agent to the nitroethane ranges from about 1:1 to about 5:1.

4. The process of claim 1, wherein ethylene is present at a pressure of about 500 psi.

5. The process of claim 1, wherein the contacting occurs in the presence of benzene.

6. The process of claim 1, wherein the contacting occurs at an elevated temperature of about 40-70° C.

7. The process of claim 1, further comprising isolating and purifying the obtained 3-methyl-2-isoxazoline.

8. The process of claim 1, further comprising contacting 3-methyl-2-isoxazoline with a reducing agent to provide a reduced product 3-amino-1-butanol.

9. The process of claim 8, wherein the reducing agent is hydrogen and hydrogenation catalyst is Raney nickel.

10. The process of claim 8, wherein the contacting occurs at an elevated temperature of about 20-100° C.

11. The process of claim 8, further comprising isolating and purifying the obtained 3-amino-1-butanol.

* * * * *